United States Patent [19]

Corday et al.

[11] Patent Number: 5,033,998

[45] Date of Patent: Jul. 23, 1991

[54] RETROGRADE DELIVERY OF PHARMACOLOGIC AND DIAGNOSTIC AGENTS VIA VENOUS CIRCULATION

[76] Inventors: Eliot Corday, 810 N. Roxbury, Beverly Hills, Calif. 90210; Samuel Meerbaum, 5741 El Canon, Woodland Hills, Calif. 91364

[21] Appl. No.: 497,767

[22] Filed: Mar. 20, 1990

Related U.S. Application Data

[60] Continuation of Ser. No. 284,757, Dec. 12, 1988, abandoned, which is a continuation of Ser. No. 87,050, Aug. 8, 1987, abandoned, which is a division of Ser. No. 785,840, Oct. 10, 1985, Pat. No. 4,689,041, which is a continuation-in-part of Ser. No. 572,411, Jan. 10, 1984, abandoned.

[51] Int. Cl.$^5$ .................... A61M 1/00; A61M 29/00
[52] U.S. Cl. ........................ 600/18; 604/53; 604/96; 604/280
[58] Field of Search ............... 600/18; 604/53, 96, 604/97, 67, 280, 281; 606/195; 128/658

[56] References Cited

U.S. PATENT DOCUMENTS

| | | | |
|---|---|---|---|
| 2,687,131 | 8/1954 | Raiche . | |
| 2,892,458 | 6/1959 | Auzin | 128/349 |
| 3,509,884 | 5/1970 | Bell . | |
| 4,154,227 | 5/1979 | Krause | 128/658 |
| 4,328,056 | 5/1982 | Snooks . | |
| 4,363,321 | 12/1982 | Chittenden . | |
| 4,411,055 | 10/1983 | Simpson et al. . | |
| 4,493,697 | 1/1985 | Krause et al. | 604/50 |
| 4,522,195 | 6/1985 | Schiff | 604/96 |
| 4,588,404 | 3/1986 | Lapeyre | 128/1 D |
| 4,648,384 | 3/1987 | Schmukler | 128/1 D |
| 4,850,969 | 7/1989 | Jackson | 604/96 |

FOREIGN PATENT DOCUMENTS

| | | |
|---|---|---|
| 8103613 | 12/1981 | PCT Int'l Appl. . |
| 2060131 | 8/1980 | United Kingdom . |

OTHER PUBLICATIONS

Samuel Meerbaum et al., "Hypothermic Coronary Venous Phased Retroperfusion: A Closed-Chest Treatment of Acute Regional Myocardial Ischemia", Circulation, vol. 65, No. 7, Jun. 1982.

Meerbaum, Samuel et al., "Retrograde Lysis of Coronary Artery Thrombus by Coronary Venous Streptokinase Administration", J AM Coll of Cardiol, 1983.

Haendchen, Roberto V. et al., "Prevention of Ischemic Injury and Early Reperfusion Derangements by Hypothermic Retroperfusion", Jam Coll of Cordiol, 1983, pp. 1067-1080.

Jean C. Farcot, et al., "Synchronized Retroperfusion of Coronary Veins for Circulatory Support of Jeopardized Ischemic Myocardium", American Journal of Cardiology, vol. 4, Jun. 1978, pp. 1191-1201.

Eliot Corday, et al., "Symposium on the Present Status of Reperfusion of the Acutely Ischemic Myocardium Part 1", American College of Cardiology, 1983; 1(4) 1031-6.

*Primary Examiner*—Randall L. Green
*Assistant Examiner*—Gary Jackson
*Attorney, Agent, or Firm*—Flehr, Hohbach, Test, Albritton & Herbert

[57] ABSTRACT

System for the retrograde delivery of fluid containing pharmacologic or diagnostic fluids to a patient's microcirculatory system through a vein which drains the microcirculatory system comprising a catheter having an inflatable balloon at the distal end thereof and adapted to be inserted into and advanced through a patient's venous system to a position in the vein which drains the microcirculatory system. The balloon is inflated to block the interior of the vein and prevent the fluid from flowing in the vein in the same direction as normal blood out-flow. Fluids containing pharmacologic or diagnostic agents are introduced through the catheter and the vein and into the microcirculatory system in a retrograde direction which is opposite to the normal blood flow therethrough. The fluid is maintained in the microcirculatory system for a minimum period and at sufficient pressure to facilitate the desired performance of the pharmacologic or diagnostic agent.

22 Claims, 2 Drawing Sheets

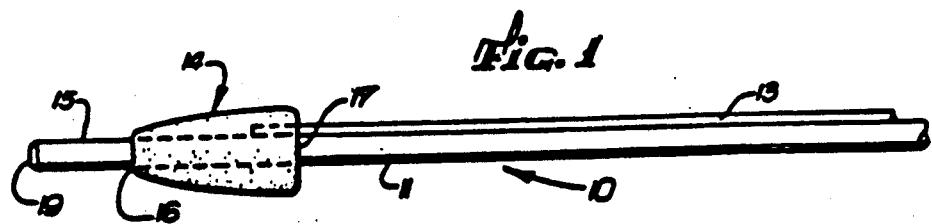
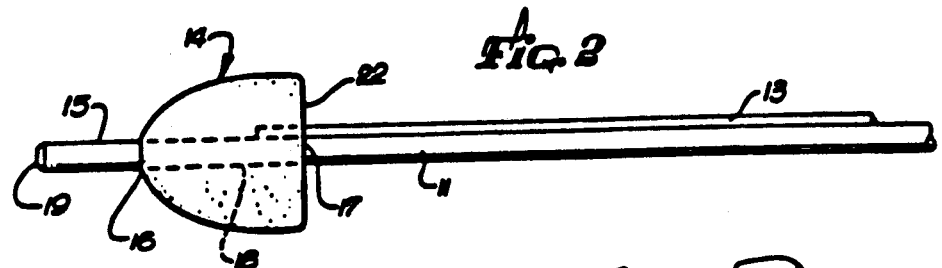
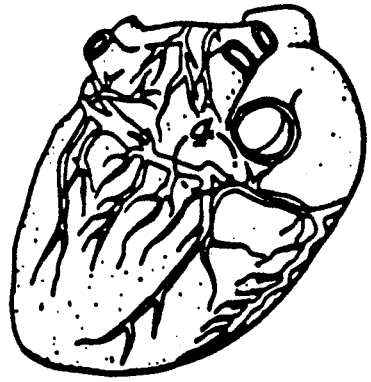

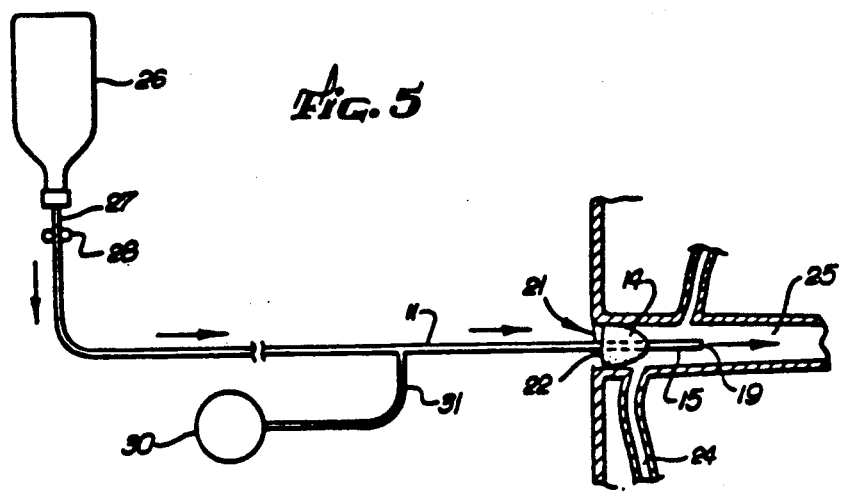
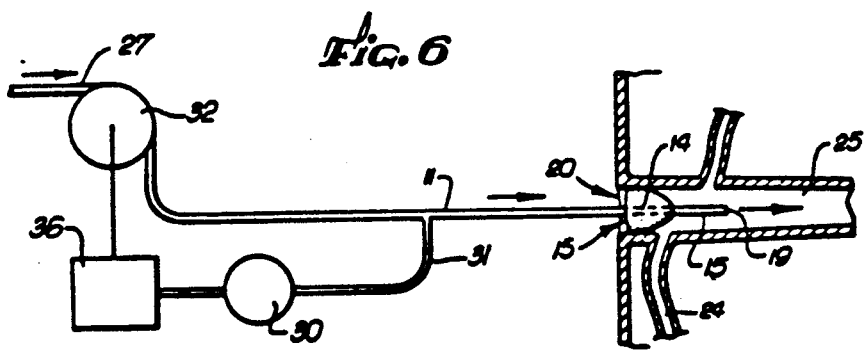
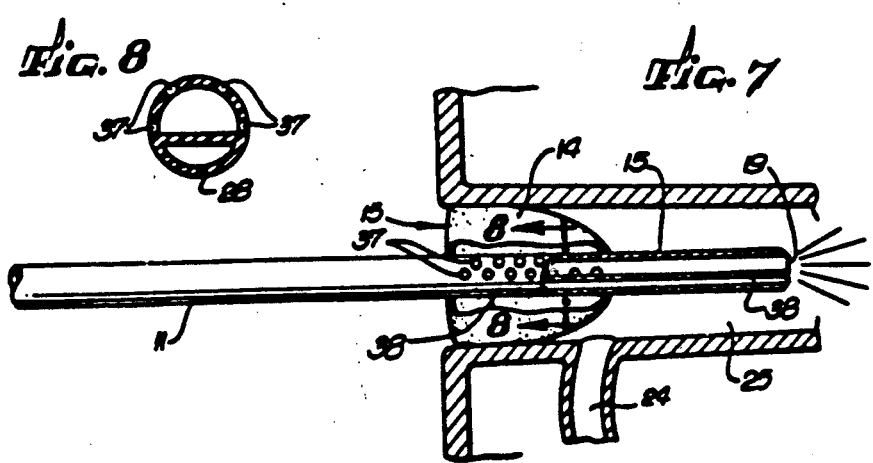

RETROGRADE DELIVERY OF PHARMACOLOGIC AND DIAGNOSTIC AGENTS VIA VENOUS CIRCULATION

This application is a continuation of application Ser. No. 07/284,757 filed Dec. 12, 1988, now abandoned, which is a continuation of application Ser. No. 07/087,050 filed Aug. 8, 1987, now abandoned, which is a division of application Ser. No. 06/785,840 filed Oct. 10, 1985, now U.S. Pat. No. 4,689,041, which is a continuation-in-part of application Ser. No. 06/572,411 filed Jan. 10, 1984, now abandoned.

BACKGROUND OF THE INVENTION

I. Field of the Invention

This invention relates generally to the use of catheters in the medical and veterinary arts and specifically to the retrograde administration of blood and other fluids containing pharmacologic or diagnostic agents through inflatable balloon catheters for the purpose of directing such agents backwards through an appropriate vein adjoining obstructed or otherwise unusable arteries which cause jeopardized circulation to vital organs. The invention is particularly directed to a controlled venous retrograde administration of oxygenated blood or other fluids to provide pharmacologic or diagnostic agents to the heart, brain, eye, kidney, liver, adrenals, or other organs with obstructed arteries thereto. This application is a continuation-in-part application of application Ser. No. 572,411 filed Jan. 10, 1984 now abandoned.

II. Reference to the Prior Art

Retroperfusion techniques for the heart, which are described in the literature, consist of the forceful delivery of arterial oxygenated blood retrogradely to the jeopardized ischemic myocardium through its adjoining coronary venous vessel in a direction opposite to the normal outflow of venous blood through that vein. This arterial blood crosses retrogradely from the coronary venous channels into the tissue capillary circulation, sometimes referred to as microcirculation, to provide blood and nourishment to an underperfused myocardium.

Coronary venous retroperfusion, as a surgical treatment for patients with coronary artery disease, was introduced by C. S. Beck in the 1940's (Beck, C. S.: Revascularization of the Heart, *Surgery*, Vol. 26, p. 82, 1949). The two-step Beck procedure consisted of creating a surgical shunt from the aorta (arterial blood) to the coronary sinus (venous circulation), and subsequently restricting the coronary sinus to facilitate effective retroperfusion of coronary veins with arterialized blood. However, long-term followup of these experiments demonstrated an unacceptable degree of myocardial and vascular damage which were apparently due to the development of excessive congestion, edema or hemorrhages resulting from interference with the coronary venous drainage, which caused permanent damage to the myocardium and led to chronic congestive failure (Beck, C. S. et al.: Operations for coronary disease, *JAMA* Vol. 13, pp. 1225-33, 1954). As a result of these considerable drawbacks and difficulties encountered at that time, coupled with rising interest in newly emerging forms of surgical revascularization of coronary arteries as a means for treatment of coronary artery disease, research in coronary sinus retroperfusion diminished.

In the 1960's, research involving surgical retroperfusion was directed at development of a modified Beck procedure consisting of a more regional coronary venous treatment of a particular zone of the heart thus curtailing the potential extent of myocardial damage due to poor coronary vein drainage.

In the 1970's, the present inventors and co-workers thereof developed a clinically oriented concept of synchronized retroperfusion designed to reduce the above hazards of myocardial edema. This was achieved by phasing of shunted arterial blood by pumping it retrogradely into coronary vein during diastole, while allowing coronary venous drainage in systole. Our experimental demonstration of synchronized retroperfusion effectiveness and safety led to renewed interest in research and application of retroperfusion. Thus, we developed a "time sharing" of the coronary veins which permitted a successful synchronized retroperfusion process with unidirectional retrograde delivery of oxygenated blood into the ischemic area, which is followed by normal coronary venous drainage and we proved that such a method could support the acutely ischemic myocardium, restore its function and reduce infarct size. We also proved that pharmacologic agents or regional cooling could be delivered along with the oxygenated blood retroperfusion. However, the need remained for a more direct and effective delivery of drugs or diagnostic materials to ischemic area where they could be absorbed over a specific time period of treatment. The present invention satisfies this need.

SUMMARY OF THE INVENTION

The present invention is directed to a method and system for the controlled directional venous retroinfusion of a variety of fluids, pharmacologic agents or diagnostic contrast solutions, either alone or in association with arterial blood. The invention provides for instillation of drugs and diagnostic agents via a retrograde alternate route for specific treatment of jeopardized ischemic tissue. Thus, an alternate neighboring venous channel is utilized to administer pharmacologic or diagnostic agents to an otherwise blockaded region made inaccessible because of an occluded artery.

The retroinfusion process and systems of the invention are designed to deliver retroinfusate comprising pharmacologic or diagnostic agents to the microcirculatory system of a region requiring treatment, and to hold the delivered retroinfusate at a controlled pressure and for a period of time which allows effective absorption and safe performance of said agents. Such delivery of the retroinfusate should, however, not unduly interfere with regional venous drainage or cause excessive pressure buildup which is associated with known deleterious effects.

Generally, it has been found that retroinfusate holding periods may be as short as about two seconds and be as long as ten minutes or more depending upon the requirements. Regional venous retroinfusion pressure limits depend for the most part on the susceptibility of the organ or area of the body being treated to pressure damage. The maximum allowable venous pressure (customarily believed to be below 50 mm Hg) depends on the period of time the pressure is to be applied, i.e., for shorter periods somewhat higher pressure levels are allowable. As an example, it is believed the appropriate systolic pressure in coronary veins and the microcirculatory system of the myocardium should not exceed 50 mm Hg for more than 5-10 minutes. After holding the retroinfusate at a desired pressure and for an appropriate period predetermined to be safe and effective, the pressure is released and the retroinfusate is allowed to drain by natural channels. The process can be repeated until the desired clinical or diagnostic effects are obtained.

The retroinfusate is delivered by means of a catheter which is passed through a patient's intact venous system in the direction of the microcirculation of the region to be treated or diagnosed. The catheter is provided with an inflatable balloon on the distal end thereof which, when inflated, anatomically conforms to the interior of the venous vessel to provide unidirectional retrograde delivery of the retroinfusate to the capillaries, and eventually into the low pressure arterial vessels in the ischemic region. The configuration of the inflated ballon may take different forms depending upon the location of its use. For example, if the catheter is to be used near the coronary sinus orifice of the heart, an acorn-shaped inflated balloon having a broad base which tapers toward the tip of the catheter is preferred. Other configurations such as sausage or dumbbell shapes may be used whenever they are more suitable for a particular vascular anatomy and for the treatment of myocardial ischemia or ectopic focal arrhythmia.

The proximal end of the catheter is provided with a connecting means adapted for coupling to external syringes, cannulae, fluid containers, or other suitable types of displacement pumping or injection devices for generally low pressure retroinfusion fluid delivery, as well as for various adaptors to provide catheter balloon inflation-deflation, sensing fluid pressures, or other measurements or sampling. The distal tip of the catheter is soft and rounded to prevent causing damage to the veins, their regional branches or any venous valves as the catheter is inserted and passed through the vessels to its ultimate destination. The inflatable balloon is non-detachably affixed about 1-4 cm proximal to the distal end of the catheter, and the balloon is structurally adapted to form an efficient seal against the inner walls of the veins when inflated.

The catheter body preferably comprises one or more hollow tubes in addition to the primary retroinfusate delivery tube. In one embodiment, a second hollow tube can be used as a means to inject or withdraw fluid for the inflation and deflation of the balloon. The distal end of this inflating tube is located inside the interior of the non-detachably secured balloon. In another embodiment, a small lumen tube is provided which passes through the balloon to the tip of the catheter, and which is operatively connected to a pressure sensing device so as to provide fluid pressure measurements within the retroinfused regional vein. In another embodiment, the distal extension of the primary retroinfusate delivery tube contains orifices within the region of and communicating with the cavity formed by the non-detachably secured balloon, which allows for direct auto-inflation of the balloon material by the retroinfusate pressure as the fluid is delivered through the primary tube into the coronary veins. In this latter embodiment, a second hollow tube may serve as the channel which is operatively connected to a pressure sensing means for monitoring of venous pressures. Additional tubes associated with the catheter may be used to provide for blood sampling or alternate measurements within the coronary veins, such as electrocardiogram, temperature monitoring or fiber-optic scope visualization of the venous system.

In a preferred embodiment, the retroinfusion catheter is inserted through the coronary sinus orifice and the catheter tip positioned so that the inflated balloon can be deployed either within the coronary sinus or its extension in the great cardiac vein. The balloon at the tip of the catheter is inflated and retroinfusate is delivered to a jeopardized underperfused myocardium for predetermined effective and safe periods, allowing adequate adsorption of the retroinfusate by the jeopardized myocardium. A pressure sensor is provided to warn if safe coronary venous pressure levels are being exceeded so that the occlusive venous balloon can be deflated and retroinfusion can be terminated. The balloon is normally deflated after the predetermined safe period (or when retroinfusate pressure exceeds maximum levels), to allow for appropriate periods of physiologic coronary venous drainage to facilitate washout of toxic metabolites via the natural venous drainage.

For cardiac treatment or diagnosis, the retroinfusate may include various agents. For example: (1) drugs such as vasodilators, inotropes, calcium antagonists, antiswelling agents, anti-inflammatory substances, substrate supplements, (2) antiarrhythmic drugs such as lidocaine, procainamide, verapamil, propranolol, disopyramide, amiodarone, and quinidine, (3) thrombolytic agents such as streptokinase, tissue plasminogen activators, (4) cardioplegics combined with regional hypothermia during cardiac surgery, coronary bypass and valve replacement, (5) various diagnostic contrast agents employed for angiography, radionuclide imaging, or contrast agents employed for echocardiographic imaging.

These and other advantages of the invention will become more apparent from the following detailed description, when considered in conjunction with the accompanying exemplary drawings.

BRIEF DESCRIPTION OF THE DRAWINGS

FIG. 1 is a schematic side view of an inflatable balloon catheter embodying features of the invention with the balloon in its deflated condition;

FIG. 2 is a schematic side view of the catheter shown in FIG. 1, but with the balloon in its inflated condition;

FIG. 3 is the posterior anatomic view of the heart showing the coronary sinus with its branches as it empties into the right atrium, highlighting the anatomical region into which the catheter is inserted;

FIG. 4 is a sectional view in the area indicated by circle 4 in FIG. 3 and shows the anatomical position of an inflated acorn-shaped balloon within the coronary sinus orifice, and its relationship to the middle cardiac vein;

FIG. 5 is a schematic view of one embodiment of this invention which depicts an elevated, gravity-fed infusion system in which the retroinfusate is controlled and delivered from a suitable sterile container via a cannula into the fluid delivery tube for ultimate delivery through a balloon catheter into the coronary sinus beyond the inflated balloon. Also shown is a pressure sensing means which monitors the pressure in the coronary vein;

FIG. 6 is a schematic view of another embodiment of this invention comprising a pump-controlled infusion apparatus which delivers the retroinfusate into the primary fluid delivery tube and which features a controller means which automatically reduces or terminates the pump flow and causes coronary sinus balloon deflation whenever the pressure sensor indicates that the coronary venous pressure exceeds a predetermined safe level.

FIG. 7 is a side view of the distal extension of the autoinflatable catheter according to one embodiment of this invention showing the orifices located in that portion of the fluid delivery tube surrounded by the balloon material and a separate interal conduit which facilitates sensing the fluid pressure in the vein.

FIG. 8 is a sectional view indicated by line 8—8 in FIG. 7.

DETAILED DESCRIPTION OF THE INVENTION

Referring to FIGS. 1 and 2, the retroinfusion catheter 10 comprises a fluid delivery tube 11 which has at its proximal end standard connecting means (not shown) adapted for coupling thereto syringes, pumps or other suitable types of infusion devices. The hollow fluid delivery tube 11 provides a channel for conveyance of retroinfusate containing pharmacologic or diagnostic agents to the diagnostic or pathologic site and a hollow secondary tube 13 runs parallel to the delivery tube 11. An inflatable balloon 14 is non-detachably secured to distal end 15 of delivery tube 11 and is sealed to it at points 16 and 17. Tube 13 is in fluid communication with the interior of balloon 14 and allows its inflation or deflation.

In order to gain retroinfusion access to the involved jeopardized region, for example the microcirculation of a heart with coronary artery obstruction, the appropriately shaped catheter 10 must be inserted through a peripheral vessel (e.g., the jugular vein in the neck) and wound through the associated venous system to a vein which communicates with the specific target area. Once the fluid delivery tube 11 is in proper position for instillation of retroinfusate into the microcirculatory system, the balloon 14 (shown deflated in FIG. 1) is inflated (as shown in FIG. 2) to provide an anatomically conforming seal against the inner walls of the vein and to cause essentially unidirectional retroinfusate delivery of the pharmacologic or diagnostic agents.

As a result of the delicate nature of the tissues in the blood vessels through which the catheter must pass, the catheter material must be flexible so as not to damage the valves or vessel walls thereof. It is particularly important that the distal end 15 of said hollow fluid delivery tube 11 be short, soft and pliable and the tip 19 be rounded, since it is this portion of the tube 11 which first comes into contact with the trauma-prone structures of the blood vessels. A suitable elastomeric material provides these desirable properties and is used for the manufacture of the catheter body. Balloon 14 is fully elastic, readily expandable and maximally foldable to prevent tissue damage as the balloon catheter is wound through the blood vessels.

FIG. 3 shows a posterior anatomical view of the heart depicting the coronary sinus and its venous branches which empty into the right atrium and the anatomical region circle 4 through which the catheter is inserted at the coronary sinus orifice.

FIG. 4 shows a magnified cutaway view of the area shown by the circle 4 in FIG. 3 and illustrates, along with FIGS. 1 and 2, the relative positions of the fluid delivery tube 11, the inflated balloon 14, and a second lumen 13 which is used to inflate the tapered balloon 14 within the coronary sinus orifice 21. The broad base 22 of balloon 14, when inflated, produces an anatomically-conforming seal against the inside of the vessel wall 23 near the coronary sinus orifice 21 without obstructing the middle cardiac vein 24. In this embodiment, the tapered shape of the inflated balloon 14 seals the coronary sinus to backflow but allows the middle cardiac vein 24 to communicate with the coronary sinus vessel, thereby limiting the pressure development within the obstructed coronary sinus 25 and preventing excessive pressure buildup which may cause myocardial edema and hemorrhages.

FIG. 5 illustrates an embodiment in which retrograde fluid delivery to the heart is facilitated by a gravity feeding infusion container 26 which dispenses a fluid containing a pharmacologic or diagnostic agent into the IV tubing 27. The quantity of retroinfusate delivered can be controlled by a flow regulator 28 located at the base of the gravity-fed infusion apparatus 26. The balloon 14 is inflated just inside the coronary sinus orifice 21 to develop a configuration with the broadened base 22 and a narrow tapered apex 29 and, thus, allow formation of a seal against the walls of coronary sinus orifice 21. After the balloon 14 is inflated, the fluid continues to flow through the primary hollow fluid delivery tube 11 and out of the distal end 15 thereof into the coronary sinus 25 for ultimate distribution and absorption at the pathological situs of the myocardium. The small secondary conduit 13 (shown in FIGS. 1, 2 and 4) provides fluid for inflating the balloon 14. A pressure sensing device 30 is provided in fluid communication through tubing 31 with the distal end 15 of delivery tube 11 to sense the pressure of the liquid at the distal end 15 of tube 11.

FIG. 6 shows another embodiment in which the fluid delivery is facilitated by a synchronous pump 32 which delivers a fluid containing pharmacologic and/or diagnostic agents from IV tubing 27 into the the hollow fluid delivery tube 11 of catheter 10 for ultimate delivery into the coronary sinus 25. In this embodiment, tubing 31 provides a passageway for communicating pressure changes in the coronary sinus 25 when the heart is in diastole to pressure sensing device 30 and a negative feedback controller 36. The pressure sensing device 30 is in operative communication with a control means 36 which is activated by pressure signals indicating excessive pressures in the coronary sinus 25 and which triggers a reduction or termination of the operation of pump 32 to thereby regulate the delivery of retroinfusate to and pressure within the coronary sinus 25.

In FIG. 7 the balloon 14 is inflated by fluid pressure from the delivery tube 11 transmitted directly through small orifices 37 provided in that portion of the hollow fluid delivery tube 11 which is surrounded by the balloon 14. While the balloon 14 is inflated, the retroinfusate is directed through the distal end 15 of the primary fluid delivery tube 11 into the coronary sinus 25. In this embodiment, a small secondary conduit 38, formed integral with delivery tube 11 as shown in FIG. 8, serves as a means through which the fluid pressure in the coronary sinus 25 can be measured when the tube 11 is operatively attached to a pressure transducer 30 as shown in FIGS. 5 and 6.

According to one aspect of the invention, when the catheter 10 is inserted into the coronary sinus orifice 21 by way of a peripheral blood vessel and the balloon 14 thereon inflated, the natural outflow of blood from the coronary sinus vessel is blocked. Drugs or diagnostic agents are injected through the hollow fluid delivery tube 11 in retrograde fashion into the coronary sinus 25 and to the situs in the microcirculation for treatment or diagnosis. Release of excessive pressure in the coronary sinus can be readily effected by deflating the balloon and thereby allowing for natural venous drainage and for the resumption of the natural anterograde blood flow from the coronary sinus 25 through the coronary sinus orifice 21 into the right atrium.

For insertion into the coronary sinus 25, the catheter balloon 14 preferably has a tapered, acorn-like configuration as shown in the drawing because this shape satisfies several possible modes of retroinfusion in the presence of different anatomical states of the coronary veins. For example, coronary artery occlusion and myocardial ischemia may affect primarily the anterior wall of the left ventricle whose coronary venous drainage is primarily subserved by the most distant portion of the coronary sinus 25 or great cardiac vein. The particular coronary venous anatomy may feature excessive coronary veno-venous shunting communications which can compromise development of sufficient intracoronary vein pressure for effective retrograde delivery of an agent into the ischemic zone. In such a case, the catheter 10 and balloon 14 is advanced via the cornary sinus deep into the region of the great cardiac vein in order to develop a higher pressure and thereby ensure retroinfusion into the specific region. In another case, where the primary ischemia is in the posterior region of the left ventricle because of circumflex coronary artery occlusion alone (or else both circumflex and left anterior descending arteries are affected by the myocardial ischemia), the catheter balloon 14 is positioned at the entrance 21 of the coronary sinus 25 with two options: 1) if there is excessive coronary veno-venous shunting, the balloon is placed into the coronary sinus 25 in a manner so as to obstruct the usually prominent middle cardiac vein 24 which is most frequently located at the beginning of the coronary sinus 25, 2) if the latter would cause too high a coronary sinus pressure during retroinfusion, the acorn shaped balloon 14 is placed at the very entrance 21 of the coronary sinus and because of its tapered shape the middle cardiac vein 24 will not be obstructed, allowing it to serve as a shunt which reduces coronary sinus pressure even while this shunted flow is effectively redirected into the coronary sinus 25 and not back into the right atrium.

One modality of the retroinfusion catheter system provides automatic control of the coronary venous blood pressure via sensing and feedback to a control system which ensures that the pressure applied for a certain period never exceeds a preset limit (for example, 50 mm Hg peak systolic blood pressure in the coronary veins during retroinfusions persisting more than 10 minutes). This control method is preferably accomplished by sensing the pressure within the coronary vein either by a sensor placed at the catheter tip or by a sensor in communication via a small lumen tube within the catheter. When the pressure exceeds the preset limit, retroinfusate injection or pumping is electronically triggered to decrease flow to a lower level or to terminate it in order to bring the coronary venous blood pressure below the prescribed limit. If the blood pressure is still elevated in spite of retroinfusion being reduced, then the coronary sinus balloon will be automatically deflated. Thus, the controlled coronary venous pressure level of retroinfusion and/or timing of coronary sinus balloon inflation provide safe conditions, avoiding undesirable engorgement of coronary veins or potential myocardial edema or hemorrhages which could lead to irreversible myocardial damage. Alternately, in a non-automatic mode, retroinfusion periods with the balloon inflated are limited to preset brief periods of less than 10 minutes, preferably less than 5 minutes, and these retroinfusion periods are separated by periods of more than 5 minutes, preferably more than 7 minutes, of balloon deflation, during which time a full coronary venous drainage and washout of accumulated toxic metabolites are ensured.

Retrograde regional venous infusion of fluids containing pharmacologic or diagnostic agents, analogous to the myocardial retroinfusion, may also be applied in the treatment of other body organs jeopardized by obstructive disease of their arterial supply or their microcirculation. By inserting a balloon tipped retroinfusion catheter via the jugular, femoral or other major vein and advancing this catheter into the regional vein which normally drains the jeopardized organ tissue, retrograde administration of appropriate drugs or diagnostic agents can be applied to treat or diagnose ischemic events of the brain and retinal circulations, the adrenals, the kidneys, the gastrointestinal tract, the liver and the extremities in accordance with the invention. The size and shape of the balloon on the catheter would probably have to be adjusted to the corresponding anatomical dimensions and blood pressure of the respective vessels through which retroinfusion is to be applied.

The catheter having a broad inflated balloon base, and tapering toward the apex thereof is described herein as being primarily utilized in the retroinfusion of drugs and diagnostic agents to the coronary sinus. The catheter may be used in the retroperfusion of oxygenated blood, including synchronized retroperfusion of such fluid, wherein the pulsatile flow of fluid is synchronized with the pulse so that fluid is pumped only during periods of coronary diastole and systolic coronary venous drainage is facilitated.

It should be apparent that other modifications and improvements can be made to this invention without departing from the scope thereof.

We claim:

1. A system for the retrograde delivery of fluid containing pharmacologic or diagnostic fluids to a microcirculatory system in a desired location within a patient's body through a vein which drains the microcirculatory system comprising:

a. a catheter having an inflatable balloon at the distal end thereof and adapted to be inserted into and advanced through a patient's venous system to a position in the vein which drains the microcirculatory system;

b. means to inflate the balloon to a size to engage the sidewalls of the vein to thereby block the interior of the vein and prevent the fluid from flowing in the vein in the same direction as normal blood out-flow;

c. means to direct fluid containing pharmacologic or diagnostic agents through the catheter and the vein and into the microcirculatory system in a retrograde direction which is opposite to the normal blood flow therethrough;

d. means for maintaining inflation of the balloon for at least two seconds so that the fluid containing pharmacologic or diagnostic agents in the microcirculatory system for a period of time of at least two seconds and at sufficient pressure to facilitate the delivery of the fluid to the desired location and the desired performance of the pharmacologic or diagnostic agent contained therein; and e. means to deflate the balloon at the distal end of the catheter to cause the balloon to move out of engagement with the sidewalls of the vein to allow the fluid to drain from the microcirculatory system through the vein in the direction of normal blood flow therein.

2. The system of claim 1, wherein means are provided to maintain the fluid in the microcirculatory system for a period of at least about 2 seconds to about 10 minutes.

3. The system of claim 2 including means to monitor fluid pressure.

4. The system of claim 3 including means to terminate or reduce fluid flow through the catheter when the means to monitor pressure indicates that the fluid pressure sensed exceeds a predetermined maximum pressure.

5. The system of claim 1, wherein means are provided to deflate the inflated balloon when the pressure of the fluid exceeds a predetermined maximum to drain fluid through the vein in the direction of normal blood flow and thereby relieve pressure.

6. The system of claim 1, wherein the inflated balloon at the distal end of the catheter has a broad base and a tapered apex.

7. The system of claim 6, wherein the inflated balloon has an acorn-like shape.

8. The system of claim 7, wherein the apex of the balloon is positioned from about 1 to 4 cm from the distal end of the catheter.

9. The system of claim 1, wherein the inflatable balloon is fixed to the outer periphery of the catheter and in a sealed relationship therewith.

10. The system of claim 9, wherein that portion of the catheter passing through the balloon is provided with one or more openings to allow for the direct pressure communication of the pharmacologic or diagnostic fluid with the interior of the balloon to thereby inflate the balloon.

11. The system of claim 10 including an electrocardiograph to determine when the heart is in diastole.

12. The system of claim 9, wherein the catheter is provided with an additional conduit which passes into and terminates in the interior of the balloon and which is adapted to direct fluid into and from the interior of the balloon to thereby inflate and deflate the balloon.

13. The system of claim 1, wherein means are provided to deliver fluid through the catheter and vein and into a microcirculatory system of the patient's myocardium when the heart thereof is in diastole.

14. The system of claim 13, wherein the means to deliver fluid through the catheter and the vein and into the microcirculatory system when the heart is in diastole includes a synchronous pump.

15. A coronary catheter comprising an elongated hollow tubular body having a fluid delivery conduit therein which is in fluid communication with an opening thereof at the proximal end of the catheter and one or more openings at the distal end thereof and an inflatable balloon close to the distal end thereof having, when inflated, a broad base generally planar portion extending radially from the hollow tubular body for a distance to occlude the vessel in which the balloon is positioned and having a forwardly extending generally tapered portion which tapers in the distal direction to the apex thereof.

16. The catheter of claim 15, wherein the apex of the balloon is disposed from about 1 to 4 cm from the distal end of the catheter.

17. The catheter of claim 15, wherein a conduit is provided integral with the tubular body which has an opening into the interior of the balloon which facilitates inflation and deflation of the balloon.

18. The catheter of claim 15, wherein the tubular body passes through the interior of the balloon and is provided with one or more openings which allow passage of fluid between the hollow tubular body and the interior of the inflatable balloon to thereby inflate or deflate the balloon.

19. The catheter of claim 15, wherein a conduit is provided integral with the tubular body which extends along a substantial length of the catheter and has an opening at the distal end of the tubular body which is in fluid communication with fluid surrounding the distal end of the catheter and having another opening at or near the proximal end of the catheter adapted to be operatively connected to a pressure sensing means whereby the pressure of the fluid at the distal end of the catheter may be sensed.

20. In a system for the retroperfusion of fluid to a jeopardized, ischemic organ or area of a patient's body which includes a catheter having an elongated hollow tubular body, means to pump fluid therethrough in a pulsatile manner with the individual pulses of fluid synchronized to occur during the heart diastole, the improvement comprising the tubular body being provided with an inflatable balloon close to the distal end thereof which, when inflated, has a broad generally planar radially extending base portion and a forwardly extending tapered portion which tapers in the distal direction to the apex thereof.

21. The system of claim 20, wherein the inflated balloon is acorn-shaped.

22. The method of claim 1 wherein the fluid containing the pharmacologic or diagnostic agent is held in the microcirculatory system for a minimum period of at least about two seconds.

* * * * *